US011653683B2

(12) United States Patent
Choi et al.

(10) Patent No.: US 11,653,683 B2
(45) Date of Patent: May 23, 2023

(54) LEUCONOSTOC MESENTEROIDES CJLM181 STRAIN PRODUCING REDUCED AMOUNT OF GAS, AND KIMCHI PRODUCTION METHOD USING SAME

(71) Applicant: CJ CHEILJEDANG CORPORATION, Seoul (KR)

(72) Inventors: Seung Hye Choi, Yongin-si (KR); Ji Young Oh, Seongnam-si (KR); Dong Yun Lee, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 396 days.

(21) Appl. No.: 16/317,075

(22) PCT Filed: Jul. 14, 2017

(86) PCT No.: PCT/KR2017/007616
§ 371 (c)(1),
(2) Date: Jan. 11, 2019

(87) PCT Pub. No.: WO2018/012942
PCT Pub. Date: Jan. 18, 2018

(65) Prior Publication Data
US 2019/0289885 A1    Sep. 26, 2019

(30) Foreign Application Priority Data

Jul. 15, 2016    (KR) .................. 10-2016-0090286

(51) Int. Cl.
| | | |
|---|---|---|
| *A23L 19/20* | (2016.01) | |
| *A23B 7/155* | (2006.01) | |
| *A23L 29/00* | (2016.01) | |
| *A23L 2/52* | (2006.01) | |
| *C12N 1/20* | (2006.01) | |
| *C12R 1/01* | (2006.01) | |

(52) U.S. Cl.
CPC .............. *A23L 19/20* (2016.08); *A23B 7/155* (2013.01); *A23L 2/52* (2013.01); *A23L 29/00* (2016.08); *C12N 1/20* (2013.01); *C12N 1/205* (2021.05); *C12R 2001/01* (2021.05); *Y02A 40/90* (2018.01)

(58) Field of Classification Search
CPC ... A23L 9/20; A23L 19/20; A23L 2/52; A23L 11/00; A23L 29/00; A23L 11/50; A23L 23/00; A23L 29/065; A23B 7/155; A23B 7/10; C12N 1/20; C12N 1/205; C12R 2001/01; Y02A 40/90; A23V 2002/00; A23Y 2260/35
See application file for complete search history.

(56) References Cited

U.S. PATENT DOCUMENTS

| | | |
|---|---|---|
| 10,123,558 B2 | 11/2018 | Kim et al. |
| 2008/0057167 A1 | 3/2008 | Byun et al. |
| 2009/0022850 A1 | 1/2009 | Oh |
| 2010/0015283 A1* | 1/2010 | Jung ................ A23B 7/024 426/49 |
| 2012/0064606 A1 | 3/2012 | Cho et al. |
| 2012/0100256 A1 | 4/2012 | Kim et al. |
| 2017/0006905 A1 | 1/2017 | Kim et al. |

FOREIGN PATENT DOCUMENTS

| | | |
|---|---|---|
| CN | 101974450 B | 5/2012 |
| CN | 102625828 B | 11/2013 |
| CN | 104894031 B | 9/2017 |
| CN | 104894029 B | 10/2017 |
| CN | 104911134 B | 7/2018 |
| JP | 2002-320473 A | 11/2002 |
| JP | 5017378 | 9/2012 |
| KR | 19990031735 A * | 5/1999 |
| KR | 10-0187828 | 6/1999 |
| KR | 10-1999-0078725 | 11/1999 |
| KR | 10-2005-0066427 | 6/2005 |
| KR | 10-2006-0046388 | 5/2006 |
| KR | 2006069719 A * | 6/2006 |
| KR | 10-2011-0007478 | 1/2011 |
| KR | 20-2013-0002058 | 9/2013 |
| KR | 10-2014-0098708 | 8/2014 |
| KR | 2015-0037269 A | 4/2015 |
| KR | 10-2016-0009702 | 1/2016 |
| KR | 10-2016-0019021 | 2/2016 |
| KR | 10-1605737 | 3/2016 |
| WO | 2006/049381 A1 | 5/2006 |
| WO | 2007/074951 A1 | 7/2007 |
| WO | 2010/101175 A1 | 9/2010 |
| WO | 2011/007924 A1 | 1/2011 |

OTHER PUBLICATIONS

Mo-Eun L, et al, Starter Cultures for Kimchi Fermentation, J. Microbiol Biotechnol (2015), 25(5), p. 559-568 (Year: 2015).*
Soetaert W, et al, A wide range of carbohydrate modifications by a single microorganism: leuconostoc mesenteroides, Progress in Biotechnology, vol. 10 (1995), p. 351-358 (Year: 1995).*
Jung JY, et al Effects of Leuconostoc mesenteroides starter cultures on microbial communities and metabolites during kimchi fermentation, International Journal of Food Microbiology (2012), 153, p. 278-287 (Year: 2012).*
Mebrouk K, et al., A new manometric method for measuring carbon dioxide production by dairy starter culture : a case of Leuconostoc mesenteroides, African Journal of Biotechnology (2006), vol. 5 (4), pp. 378-383 (Year: 2006).*

(Continued)

*Primary Examiner* — Donald R Spamer
*Assistant Examiner* — Jeffrey D Benson
(74) *Attorney, Agent, or Firm* — Renner, Otto, Boisselle & Sklar, LLP

(57) ABSTRACT

The present application relates to a *Leuconostoc mesenteroides* CJLM181 strain (KCTC 13042BP) producing decreased amounts of gas, a fermentation starter composition comprising the same, and a method for preparing kimchi using the strain.

7 Claims, No Drawings
Specification includes a Sequence Listing.

(56) References Cited

OTHER PUBLICATIONS

In-Kwon Choi et al., "Novel Leuconostoc citreum starter culture system for the fermentation of kimchi, a fermented cabbage product", Antonie Van Leeuwenhoek, 2003, vol. 84, No. 4, pp. 247-253, XP008148164.
Jong-Hoon Lee, "Current studies on the community of lactic acid bacteria in Kimchi—a traditional Korean fermented food-", Milk Science, 2009, vol. 58, No. 3, pp. 153-159.
Extended European Search Report for corresponding European Patent Application No. 17828012.9 dated Jan. 8, 2020.
Jin Hongxing et al., "Screening and Identification of Leuconostoc in Kimchi", China Brewing, No. 8, Dec. 31, 2009, pp. 82-84 (with English abstract on the first page).
Original Office Action issued for corresponding Chinese National Stage Application No. 201780043644, dated Nov. 1, 2022.

\* cited by examiner

LEUCONOSTOC MESENTEROIDES CJLM181 STRAIN PRODUCING REDUCED AMOUNT OF GAS, AND KIMCHI PRODUCTION METHOD USING SAME

TECHNICAL FIELD

The present application relates to a *Leuconostoc mesenteroides* strain producing decreased amounts of gas and a method for preparing kimchi using the same.

BACKGROUND ART

Kimchi is a food prepared by the fermentative action of microorganisms, in which the microorganisms may act to degrade the components of the food and synthesize new components to improve the nutritive value, preference and storage stability of the food.

Conventional kimchi has problems in that gas (mainly carbon dioxide) is produced during distribution of kimchi to cause package inflation, damage to the package, and leakage from the package, and in that the taste quality of kimchi is reduced due to a strong sour taste resulting from overaging.

To overcome such problems, control methods using various packaging technologies such as a polymer film having high gas permeability (Korean Patent Application Publication No. 10-1999-0078725) or application of a one-way valve (Korean Utility Model Publication No. 20-2013-0002058) were reported. However, these methods have limitations in terms of costs or the like in their actual commercialization, and fail to provide a fundamental solution to changes in quality of kimchi, such as a strong sour taste resulting from overaging.

Under this background, the present inventors have made extensive studies to develop a method capable of reducing gas production in the preparation of kimchi. As a result, the present inventors have found that when kimchi is prepared using a specific *Leuconostoc mesenteroides* strain, gas production can be decreased while inhibiting an increase in sour taste, thereby completing the present application.

PRIOR ART DOCUMENTS

Patent Documents

Patent Document 1: KR 10-1999-0078725 A (1999Nov. 5);
Patent Document 2: KR 20-2013-0002058 A (2013Apr. 2).

DISCLOSURE

Technical Problem

It is an object of the present application to provide a *Leuconostoc mesenteroides* CJLM181 strain (KCTC 13042BP) producing decreased amounts of gas.

Another object of the present application is to provide a fermentation starter composition comprising the *Leuconostoc mesenteroides* CJLM181 strain.

Still another object of the present application is to provide kimchi comprising the *Leuconostoc mesenteroides* CJLM181 strain or the fermentation starter composition of the present application.

Yet another object of the present application is to provide a method for preparing kimchi, comprising a step of bringing the *Leuconostoc mesenteroides* CJLM181 strain or the fermentation starter composition of the present application into contact with a material to be fermented.

Technical Solution

Hereinafter, the present application will be described in detail. Meanwhile, the description of one aspect and embodiment disclosed in the present application may also be applied to other aspects and embodiments with respect to common elements. Moreover, all combinations of various elements disclosed in the present application fall within the scope of the present application. In addition, it does not appear that the scope of the present application is limited by the following detailed description.

To achieve the objects of the present application, in one aspect, the present application provides a *Leuconostoc mesenteroides* CJLM181 strain (KCTC 13042BP) producing decreased amounts of gas. The *Leuconostoc mesenteroides* CJLM181 strain (KCTC 13042BP) of the present application may be *Leuconostoc mesenteroides* subsp. *Mesenteroides*.

According to other embodiments of the present application, the strain of the present application may be a strain producing decreased amounts of acid. Specifically, the acid in the present application may be lactic acid. Thus, when kimchi is prepared using the strain of the present application, the taste quality of kimchi can be maintained by inhibiting an increase in sour taste, compared to when kimchi is prepared using other *Leuconostoc mesenteroides* strains.

According to another embodiment of the present application, the strain of the present application may be a strain producing increased amounts of mannitol. Mannitol gives a cooling feeling and a refreshing taste to kimchi, suppresses sour taste, and also inhibit the proliferation of over-acidifying microorganisms to prevent kimchi from being excessively fermented.

According to still another embodiment of the present application, the strain of the present application showed negative results in all gelatin liquefaction, toxic metabolite (e.g., ammonia) production, phenylalanine deaminase production, and hemolysis tests, indicating that it is safe even when it is applied to food (see Example 5).

According to still another embodiment of the present application, the strain of the present application may comprise 16s rRNA comprising a sequence of SEQ ID NO: 1.

The *Leuconostoc mesenteroides* CJLM181 strain of the present application may comprise a cell wall fragment, living cell or dried cell of the strain.

In another aspect, the present application provides A fermentation starter composition comprising a *Leuconostoc mesenteroides* CJLM181 strain (KCTC 13042BP) or a culture thereof.

The fermentation starter composition of the present application may comprise the *Leuconostoc mesenteroides* CJLM181 strain (KCTC 13042BP) of the present application at a concentration of $10^7$ cfu/ml or more, specifically, $10^7$ cfu/ml to $10^{13}$ cfu/ml, or $10^9$ cfu/ml to $10^{12}$ cfu/ml.

As used herein, the term "culture" means a material resulting from culture of the *Leuconostoc mesenteroides* CJLM181 strain (KCTC 13042BP) of the present application after inoculation into medium. Specifically, the culture of the present application may include a culture itself obtained by culturing the strain of the present application (that is, the culture may include the *Leuconostoc mesenteroides* CJLM181 strain (KCTC 13042BP) of the present application, medium or a metabolic product of the strain), a filtrate (e.g., a centrifuged supernatant) obtained by filtering or centrifuging the culture to remove the strain, or the like. In addition, the culture of the present application may include one obtained by drying (e.g., freeze-drying) and powdering the culture.

According to one embodiment of the present application, culturing in the present application may be performed at a temperature of 10° C. to 30° C. for 6 to 48 hours. Specifically, the culturing may be performed at a temperature of 20° C. to 30° C. for 12 to 36 hours or 18 to 30 hours.

The medium that is used in the present application is not limited and may be any known medium for lactic acid bacteria. Specifically, the medium that is used in the present application may include a carbon source and a nitrogen source. More specifically, the carbon source may be one or more selected from the group consisting of sucrose, glucose and fructose, and the nitrogen source may be one or more selected from the group consisting of yeast extract, peptone, beef extract, malt extract, corn steep liquor, ammonium citrate, ammonium sulfate, ammonium chloride, ammonium phosphate, ammonium carbonate, and ammonium nitrate. The medium that is used in the present application may further include one or more selected from the group consisting of Tween 80, sodium citrate, potassium phosphate, sodium acetate, manganese sulfate, magnesium sulfate, and distilled water.

As used herein, the term "fermentation starter" means an agent that is artificially applied to a material to be fermented in order to support the start of fermentation.

According to one embodiment of the present application, the fermentation starter composition may be in a liquid or powder form.

According to other embodiments of the present application, the fermentation starter composition of the present application may further comprise a cryoprotectant. More specifically, the fermentation starter composition may further comprise one or more cryoprotectants selected from the group consisting of glycerol, trehalose, maltodextrin, powdered skim milk, and starch. The cryoprotectant that is used in the present application may be comprised in an amount of 0.01 wt % to 20 wt %, or 0.01 wt % to 10 wt %, based on the total weight of the fermentation starter composition of the present application. Specifically, in the present application, glycerol may be comprised in an amount of 5 to 20 wt % in the fermentation starter composition; trehalose may be comprised in an amount of 2 to 10 wt % in the fermentation starter composition; powdered skim milk may be comprised in an amount of 0.5 to 2 wt % in the fermentation starter composition; and starch may be comprised in an amount of 0.1 to 1 wt % in the fermentation starter composition.

According to another embodiment of the present application, the fermentation starter composition of the present application may further comprise an excipient. Specifically, the excipient that is used in the present application may be one or more selected from the group consisting of glucose, dextrin and powdered skim milk. More specifically, the excipient that is used in the present application may be comprised in an amount of 75 to 95 wt %, or 85 to 95 wt %, based on the total weight of the fermentation starter composition of the present application.

In still another aspect, the present application provides kimchi comprising the *Leuconostoc mesenteroides* CJLM181 strain (KCTC 13042BP) of the present application or the fermentation starter composition of the present application.

As used herein, the term "kimchi" means a food obtained by salting vegetables (e.g., Chinese cabbage, radish, green onion, leaf mustard and cucumber, etc.) and adding seasonings (e.g., red pepper powder, garlic, ginger and pickled fish, etc.) to the salted vegetables, followed by fermentation.

The kimchi of the present application may further comprise known food-acceptable additives. Specifically, the kimchi of the present application may further comprise natural fragrance such as plum fragrance, lemon fragrance, pine apple fragrance, herb fragrance or the like; natural pigment such as natural fruit juice, chlorophyllin, flavonoid or the like; a sweetening component such as fructose, honey, sugar alcohol or sugar; or an acidulant such as citric acid or sodium citrate.

In still another aspect, the present application provides a method for preparing kimchi, comprising a step of bringing the *Leuconostoc mesenteroides* CJLM181 strain (KCTC 13042BP) of the present application or the fermentation starter composition of the present application into contact with a material to be fermented.

According to other embodiments of the present application, the *Leuconostoc mesenteroides* CJLM181 strain (KCTC 13042BP) of the present application or the fermentation starter composition of the present application may be brought into contact with a material to be fermented in an amount of 0.01 to 3 wt %, 0.1 to 3 wt %, 0.5 to 3 wt %, or 0.5 wt % to 2 wt %, based on the total weight of the material to be fermented.

In addition, the contacting in the present application may be performed at a temperature of 3 to 10° C. or 5 to 10° C. for 1 to 90 days, 10 to 90 days, 10 to 60 days, 20 to 60 days, or 20 to 40 days.

In still another aspect, the present application provides kimchi prepared by the method for preparing kimchi according to the present application.

Advantageous Effects

The *Leuconostoc mesenteroides* CJLM181 strain (KCTC 13042BP) of the present application produces decreased amounts of gas. Thus, when kimchi is prepared using the strain or a culture thereof as a fermentation starter, gas production during distribution of the kimchi can be decreased, and thus problems such as damage to packages by gas production can be prevented from arising, thereby stabilizing the distribution quality of the kimchi. Furthermore, the strain of the present application produces decreased amount of acid, and thus maintains constant acidity. In addition, the strain of the present application has an excellent ability to produce mannitol, and thus is effective in improving the taste quality of kimchi.

MODE FOR INVENTION

Hereinafter, the present application will be described in further detail with reference to examples. It is to be understood, however, that these examples are provided for better understanding of the present application and are not intended to limit the scope of the present application in any way.

Example 1: Isolation of Strain Producing Decreased Amounts of Gas 1-1) Strain Isolation and Identification Various kinds of kimchi purchased from supermarkets were aged at a low temperature of 5° C., and kimchi that reached a pH ranging from 3.8 to 4.5 was used as a kimchi sample. The kimchi sample was diluted 10-fold with 0.85% saline, inoculated onto a PES agar medium (phenyl ethyl alcohol sucrose agar; per liter of distilled water, 5 g of trypton, 0.5 g of yeast extract, 20 g of sucrose, 2 g of ammonium sulfate, 1 g of potassium phosphate dibasic, 0.244 g of magnesium sulfate, 2.5 ml of phenyl ethyl alcohol, and 15 g of agar) plate, and spread using a spreader. Next, the plate was incubated in an incubator at 25° C. for 24 hours, and then each produced colony was streaked onto a separate agar plate and separated into single colonies.

1-2) Selection of Strains Producing Decreased Amounts of Gas

Each of the strain colonies separated in Example 1-1 above was inoculated into 10 ml of MRS broth (Difco MRS broth; 10 g of bacto peptone, 10 g of beef extract, 5 g of yeast extract, 20 g of glucose, 1 g of Tween 80, 2 g of ammonium citrate, 2 g of potassium phosphate dibasic, 5 g of sodium acetate, 0.1 g of manganese sulfate, 0.05 g of magnesium sulfate, and 1 L of distilled water) in a test tube comprising a 30 mm-height Durham tube, and then was stationary-cultured at 25° C. for 24 hours. The height of gas trapped in the Durham tube was measured to determine the production of gas, and strains showing a gas production of 10 mm or lower were selected.

1-3) Selection of Strains Producing Decreased Amounts of Acid

Each of the strain colonies selected in Example 1-2 above was inoculated onto 10 ml of MRS broth (Difco MRS broth; 10 g of bacto peptone, 10 g of beef extract, 5 g of yeast extract, 20 g of glucose, 1 g of Tween 80, 2 g of ammonium citrate, 2 g of potassium phosphate dibasic, 5 g of sodium acetate, 0.1 g of manganese sulfate, 0.05 g of magnesium sulfate, and 1 L of distilled water). For measurement of acid production, each colony was stationary-cultured at 25° C. for 24 hours, and then measured for its pH using a pH meter (SevenCompact/Ion S220, Mettler Toledo), and strains having a pH of 4.39 or higher were selected.

1-4) Selection of Strain Producing Increased Amounts of Mannitol

Each of the strain colonies selected in Example 1-3 above was inoculated into 10 ml of minimal medium (10 g of bacto peptone, 20 g of fructose, 1 g of Tween 80, 2 g of ammonium citrate, 2 g of potassium phosphate dibasic, 5 g of sodium acetate, 0.1 g of manganese sulfate, 0.05 g of magnesium sulfate, and 1 L of distilled water) containing 2% fructose, and was stationary-cultured at 25° C. for 24 hours, followed by measurement of the amount of mannitol produced. The amount of mannitol produced was measured by HPLC, and a strain showing a mannitol production of 16,000 mg/L or more was selected.

1-5) Identification of Selected Strain

The strain selected in Example 1-4 above was named "CJLM181", and the 16s rRNA nucleotide sequence thereof (SEQ ID NO: 1) was analyzed. As a result, it could be seen that the 16s rRNA nucleotide sequence of the CJLM181 strain was 99% identical to the 16s rRNA nucleotide sequence of *Leuconostoc mesenteroides* subsp. *Mesenteroides* CCMMB1121 (SEQ ID NO: 2). Accordingly, the CJLM181 strain was named "*Leuconostoc mesenteroides* CJLM181", and deposited in the Korean Collection for Type Cultures at the Korea Research Institute of Bioscience and Biotechnology on Jun. 10, 2016 under accession number KCTC 13042BP.

Example 2: Comparison of Gas Production

In order to compare the production of gas by *Leuconostoc mesenteroides* CJLM181 selected in Example 1 with those of other *Leuconostoc mesenteroides* strains, *Leuconostoc mesenteroides* KCTC3100 and KCTC3722 that are *Leuconostoc mesenteroides* standard strains were used as control strains to measure gas production. Each strain was inoculated into 10 ml of MRS broth in a test tube comprising a 30 mm-height Durham tube, and was cultured at 25° C. for 24 hours, after which the height of gas trapped in the Durham tube was measured and gas production was compared. Gas generation was rated according to the following criteria: "−"=no gas production; "+"=the height of gas trapped in the Durham tube is 1 to 5 mm; "++"=the height of gas is 6 to 10 mm; "+++"=the height of gas is 11 to 15 mm; "++++"=the height of gas is 16 to 25 mm; and "+++++"=the height of gas is higher than 25 mm.

As a result, it was shown that the gas production of *Leuconostoc mesenteroides* CJLM181 was "++", which was significantly lower than the gas production of the control strains ("++++" or "+++") (Table 1).

TABLE 1

|  | *Leuconostoc mesenteroides* CJLM181 | *Leuconostoc mesenteroides* KCTC3100 | *Leuconostoc mesenteroides* KCTC3722 |
|---|---|---|---|
| Gas production | ++ | ++++ | +++ |

Example 3: Comparison of Acid Production

The production of acid by *Leuconostoc mesenteroides* CJLM181 selected in Example 1 was compared with those of *Leuconostoc mesenteroides* KCTC3100 and KCTC3722 which are control strains. Each of the strains was inoculated into 10 ml of MRS broth. For measurement of acid production, each strain was stationary-cultured at 25° C. for 24 hours, and then measured for its pH using a pH meter (SevenCompact/Ion S220, Mettler Toledo).

As a result, it was shown that the acid production of *Leuconostoc mesenteroides* CJLM181 was significantly lower than that of the control strains (Table 2).

TABLE 2

|  | *Leuconostoc mesenteroides* CJLM181 | *Leuconostoc mesenteroides* KCTC3100 | *Leuconostoc mesenteroides* KCTC3722 |
|---|---|---|---|
| Ph | 4.39 | 4.33 | 4.37 |

Example 4: Comparison of Mannitol Production

The production of mannitol by *Leuconostoc mesenteroides* CJLM181 selected in Example 1 was compared with those of *Leuconostoc mesenteroides* KCTC3100 and KCTC3722 which are control strains. Each of the strains was inoculated into 10 ml of minimal medium (10 g of bacto peptone, 20 g of fructose, 1 g of Tween 80, 2 g of ammonium citrate, 2 g of potassium phosphate dibasic, 5 g of sodium acetate, 0.1 g of manganese sulfate, 0.05 g of magnesium sulfate, and 1 L of distilled water) containing 2% fructose, and was cultured at 25° C. for 24 hours, after which the content of mannitol in the supernatant was measured by HPLC.

As a result, it was shown that the production of mannitol by *Leuconostoc mesenteroides* CJLM181 increased 146% and 185% compared to those of the control strains, respectively (Table 3).

TABLE 3

| | Leuconostoc mesenteroides CJLM181 | Leuconostoc mesenteroides KCTC3100 | Leuconostoc mesenteroides KCTC3722 |
|---|---|---|---|
| Mannitol production (mg/L) | 16336.34 | 11224.70 | 8815.10 |

Example 5: Evaluation of Safety of Strain

In order to examine whether or not *Leuconostoc mesenteroides* CJLM181 selected in Example 1 would be used as a starter in preparation of kimchi, the safety of the strain was analyzed. Specifically, according to the safety evaluation testing methods proposed in the Korean Bio Venture Association Standards, hemolysis, gelatin liquefaction, toxic metabolic (ammonia) production and phenylalanine deaminase tests were performed.

As a result, it was shown that the *Leuconostoc mesenteroides* CJLM181 strain showed negative results in all the hemolysis, gelatin liquefaction, toxic metabolic (ammonia) production and phenylalanine deaminase tests, indicating that it is a safe strain that may be administered to the human body and may be used in the preparation of food (Table 4).

TABLE 4

| Gelatin liquefaction test | Phenylalanine deaminase test | Hemolysis test | Ammonia production |
|---|---|---|---|
| Negative | Negative | γ | Negative |

*γ (gamma-hemolysis): no hemolysis.

Example 6: Preparation of Kimchi 6-1) Preparation of Kimchi Using *Leuconostoc mesenteroides* CJLM181

A medium was prepared by mixing 2.5 g of sucrose, 1.0 g of trisodium citrate, 1.5 g of peptone, 1.0 g of glucose, 1.0 g of yeast extract, 0.5 g of fructose, 0.5 g of sodium acetate and 1 L of distilled water, followed by sterilization. About $10^9$ CFU/ml of the *Leuconostoc mesenteroides* CJLM181 strain was inoculated into the medium in an amount of 1 wt % based on the total weight of the medium, and cultured at 25° C. for 24 hours, thereby preparing a strain culture. Next, the prepared strain culture was added to a general kimchi seasoning (obtained by mixing red pepper powder (2.5 wt %), garlic (2 wt %), ginger (0.4 wt %), green onion (1 wt %), radish (18 wt %) and fish sauce (5 wt %)) in an amount of 0.1 wt % based on the total weight of kimchi to prepare a seasoning. Then, the prepared seasoning was mixed with salted Chinese cabbage, thereby preparing kimchi (Experimental Example 1).

6-2) Preparation of Kimchi Using Standard Strain Culture

Kimchi was prepared in the same manner as described in Example 6-1, except that a culture of each of *Leuconostoc mesenteroides* standard strains KCTC3100 and KCTC3722 was used (use of KCTC3100 culture: Comparative Example 1; use of KCTC3722 culture: Comparative Example 2).

6-3) Preparation of Kimchi without Addition of Strain Culture

Kimchi (Comparative Example 3) was prepared in the same manner as described in Example 6-1 above, except that the strain culture was not added to the kimchi seasoning.

Example 7: Analysis of Characteristics of Kimchi 7-1) Comparison of Acid Production The kimchi of each of Experimental Example 1 and Comparative Examples 1 to 3 was stored at 7° C. for 30 days, and lactic acid production in each kimchi was measured. Specifically, a predetermined amount of each kimchi was crushed, and then filtered through gauze to prepare kimchi juice. To analyze the amount of lactic acid in the kimchi juice, 3 ml of the kimchi juice was taken, centrifuged (at 10,000 g for 10 minutes), and filtered through a 0.2 μm filter, and then the components thereof were analyzed by HPLC.

As a result, it could be seen that lactic acid production in the kimchi of Experimental Example 1 was 70 to 75% of lactic acid production in each of the kimchi of Comparative Example 3, prepared without using the strain culture, and of the kimchi samples of Comparative Examples 1 and 2, prepared using the standard strain cultures. This suggests that when kimchi is prepared using a culture of the *Leuconostoc mesenteroides* CJLM181 strain, an increase in sour taste can be inhibited to maintain the taste quality of the kimchi (Table 5).

TABLE 5

| | Experimental Example 1 | Comparative Example 1 | Comparative Example 2 | Comparative Example 3 |
|---|---|---|---|---|
| Lactic acid production (mg/L) | 5382.4 | 7379.2 | 7198.2 | 7585.4 |

7-2) Comparison of Gas Production

A predetermined amount of the kimchi of each of Experimental Example 1 and Comparative Examples 1 to 3 was placed in an A1 pouch without a gas absorbent and stored at 7° C. for 30 days, and an increase in the volume was measured to determine the gas production in each kimchi.

As a result, gas production in the kimchi of Experimental Example 1 is 37 to 41% of gas production in the kimchi of Comparative Examples 1 and 2, prepared using the standard strain cultures, and was lower than the kimchi of Comparative Example 3, prepared without using any strain culture. This suggests that when kimchi is prepared using a culture of the *Leuconostoc mesenteroides* CJLM181 strain, gas production in the kimchi can be significantly decreased to thereby increase convenience during distribution of the kimchi (Table 6).

TABLE 6

| | Experimental Example 1 | Comparative Example 1 | Comparative Example 2 | Comparative Example 3 |
|---|---|---|---|---|
| Gas generation (cc/g) | 0.95 | 2.54 | 2.33 | 2.02 |

7-3) Comparison of Mannitol Production

The kimchi of each of Experimental Example 1 and Comparative Examples 1 to 3 was stored at 7° C. for 30 days, and mannitol production in each kimchi was measured. Specifically, a predetermined amount of each kimchi was crushed, and then filtered through gauze to prepare kimchi juice. 3 ml of the kimchi juice was taken, centrifuged (at 10,000 g for 10 minutes), and filtered through a 0.2 μm filter, and then the components thereof were analyzed by HPLC.

As a result, it could be seen that mannitol production in the kimchi of Experimental Example 1 was 172 to 176% of mannitol production in the kimchi of Comparative Example 3, prepared without using any strain culture, and the kimchi of Comparative Examples 1 and 2, prepared using the standard strain cultures. This suggests that when kimchi is prepared using a culture of the *Leuconostoc mesenteroides* CJLM181 strain, the prepared kimchi may contain a large amount of mannitol, and thus have excellent storage stability and taste quality (Table 7).

TABLE 7

| | Experimental Example 1 | Comparative Example 1 | Comparative Example 2 | Comparative Example 3 |
|---|---|---|---|---|
| Mannitol production (mg/L) | 16553.4 | 9418.8 | 9628.7 | 8099.8 |

Accession Number

Name of Depositary Institution: Korea Research Institute of Bioscience and Biotechnology;

Accession Number: KCTC 13042BP;

Date of Deposit: Jun. 10, 2016.

The invention claimed is:

1. A fermentation starter composition comprising:
Leuconostoc mesenteroides CJLM181 strain KCTC 13042BP or culture thereof; and one or more cryoprotectants;
wherein the Leuconostoc mesenteroides CJLM181 strain KCTC 13042BP comprises 16s rRNA nucleotide sequence encoded by the nucleotide sequence of SEQ ID NO:1.

2. The fermentation starter composition of claim 1, comprising the Leuconostoc mesenteroides CJLM181 strain KCTC 13042BP at a concentration of $10^7$ cfu/ml or more.

3. Kimchi prepared by using the fermentation starter composition of claim 1, wherein the fermentation starter composition comprises the Leuconostoc mesenteroides CJLM181 strain KCTC 13042BP at a concentration of $10^7$ cfu/ml or more.

4. A method for preparing kimchi, comprising a step of bringing the Leuconostoc mesenteroides CJLM181 strain KCTC 13042BP into contact with a material to be fermented;
wherein the Leuconostoc mesenteroides CJLM181 strain KCTC 13042BP comprises 16s rRNA nucleotide sequence encoded by the nucleotide sequence of SEQ ID NO:1.

5. Kimchi prepared by using the fermentation starter composition of claim 2.

6. A method for preparing kimchi, comprising a step of bringing the fermentation starter composition of claim 1 into contact with a material to be fermented.

7. A method for preparing kimchi, comprising a step of bringing the fermentation starter composition of claim 2 into contact with a material to be fermented.

* * * * *

SEQUENCE LISTING

<160> NUMBER OF SEQ ID NOS: 2

<210> SEQ ID NO 1
<211> LENGTH: 986
<212> TYPE: DNA
<213> ORGANISM: Unknown
<220> FEATURE:
<223> OTHER INFORMATION: Genes for 16S rRNA of Leuconostoc mesenteroides CJLM181

<400> SEQUENCE: 1

```
aaaagttcgg gtctccagcg gacacttaat gcgttagctt cggcactaag aggcggaaac      60
ctcctaacac ctagtgttca tcgtttacgg tgtggactac cagggtatct aatcctgttt     120
gctacccaca ctttcgagcc tcaacgtcag ttgcagtcca gtaagccgcc ttcgccactg     180
gtgttcttcc atatatctac gcattccacc gctacacatg gagttccact tacctctact     240
gcactcaagt taaccagttt ccaatgccat tccggagttg agctccgggc tttcacatca     300
gacttaataa accgtctgcg ctcgctttac gcccaataaa tccggataac gctcgggaca     360
tacgtattac cgcggctgct ggcacgtatt tagccgtccc tttctggtat ggtaccgtca     420
aactaaaatc atttcctatt ctagctgttc ttcccataca acagtgcttt acgacccgaa     480
agccttcatc acacacgcgg cgttgctcca tcaggctttc gcccattgtg gaagattccc     540
tactgcagcc tcccgtagga gtttgggccg tgtctcagtc ccaatgtggc cgatcagtct     600
ctcaactcgg ctatgcatca ttgtcttggt aggcctttac cccaccaact aactaatgca     660
ccgcggatcc atctctaggt gacgccgaag cgccttttaa ctttttgtca tgcgacacta     720
agttttattc ggtattagca tctgtttcca aatgttatcc ccagccttga ggcaggttgt     780
ccacgtgtta ctcacccgtt cgccactcac ttgaaaggtg caagcacctt tcgctgtgcg     840
ttcgacttgc atgtattagg cacgccgcca gcgttcatcc tgacagagaa aaaaaaacta     900
tataaagggt tttggggtaa aattttttaag gaatttaggg accaaaggta aaaagcttaa     960
aagggttccc tggttaccga tgtttg                                          986
```

<210> SEQ ID NO 2
<211> LENGTH: 1514
<212> TYPE: DNA
<213> ORGANISM: Unknown
<220> FEATURE:
<223> OTHER INFORMATION: Genes for 16S rRNA of Leuconostoc mesenteroides subsp. mesenteroides strain CCMMB1121

<400> SEQUENCE: 2

```
gctcaggatg aacgctggcg gcgtgcctaa tacatgcaag tcgaacgcac agcgaaaggt       60
```

-continued

```
gcttgcacct ttcaagtgag tggcgaacgg gtgagtaaca cgtggacaac ctgcctcaag        120
gctggggata acatttggaa acagatgcta ataccgaata aaacttagtg tcgcatgaca        180
aaaagttaaa aggcgcttcg gcgtcaccta gagatggatc cgcggtgcat tagttagttg        240
gtggggtaaa ggcctaccaa gacaatgatg catagccgag ttgagagact gatcggccac        300
attgggactg agacacggcc caaactccta cgggaggctg cagtagggaa tcttccacaa        360
tgggcgaaag cctgatggag caacgccgcg tgtgtgatga aggctttcgg gtcgtaaagc        420
actgttgtat gggaagaaca gctagaatag gaaatgattt tagtttgacg gtaccatacc        480
agaaagggac ggctaaatac gtgccagcag ccgcggtaat acgtatgtcc cgagcgttat        540
ccggatttat tgggcgtaaa gcgagcgcag acggtttatt aagtctgatg tgaaagcccg        600
gagctcaact ccggaatggc attggaaact ggttaacttg agtgcagtag aggtaagtgg        660
aactccatgt gtagcggtgg aatgcgtaga tatatgaag aacaccagtg gcgaaggcgg        720
cttactggac tgcaactgac gttgaggctc gaaagtgtgg gtagcaaaca ggattagata        780
ccctggtagt ccacaccgta aacgatgaac actaggtgtt aggaggtttc cgcctcttag        840
tgccgaagct aacgcattaa gtgttccgcc tggggagtac gaccgcaagg ttgaaactca        900
aaggaattga cggggacccg cacaagcggt ggagcatgtg gtttaattcg aagcaacgcg        960 aagaaccta ccaggtcttg acatcctttg aagcttttag agatagaagt gttctcttcg        1020
gagacaaagt gacaggtggt gcatggtcgt cgtcagctcg tgtcgtgaga tgttgggtta        1080
agtcccgcaa cgagcgcaac ccttattgtt agttgccagc attcagatgg gcactctagc        1140
gagactgccg gtgacaaacc ggaggaaggc ggggacgacg tcagatcatc atgcccctta        1200
tgacctgggc tacacacgtg ctacaatggc gtatacaacg agttgccaac ccgcgagggt        1260
gagctaatct cttaaagtac gtctcagttc ggattgtagt ctgcaactcg actacatgaa        1320
gtcggaatcg ctagtaatcg cggatcagca cgccgcggtg aatacgttcc cgggtcttgt        1380
acacaccgcc cgtcacacca tgggagtttg taatgcccaa agccggtggc ctaacctttt        1440
aggaaggagc cgtctaaggc aggacagatg actggggtga agtcgtaaca aggtagccgt        1500
aggagaacct gcgg                                                          1514
```